(12) United States Patent
Messer et al.

(10) Patent No.: US 6,211,204 B1
(45) Date of Patent: Apr. 3, 2001

(54) MUSCARINIC RECEPTOR AGONISTS

(75) Inventors: William S. Messer; Yang Cao, both of Toledo, OH (US); Walajapet G. Rajeswaran, Metairie, LA (US)

(73) Assignee: University of Toledo, Toledo, OH (US)

( * ) Notice: Subject to any disclaimer, the term of this patent is extended or adjusted under 35 U.S.C. 154(b) by 0 days.

(21) Appl. No.: 09/483,334

(22) Filed: Jan. 14, 2000

Related U.S. Application Data

(63) Continuation-in-part of application No. 09/236,030, filed on Jan. 22, 1999, now Pat. No. 6,096,767.

(51) Int. Cl.$^7$ .......................... A61K 31/34; C07D 417/00

(52) U.S. Cl. .................. 514/342; 546/187; 546/268.7

(58) Field of Search ................. 546/187, 268.7; 514/342

(56) References Cited

FOREIGN PATENT DOCUMENTS 0 384 288 A2   8/1990   (EP) .
WO93/14089     7/1993   (WO) .

OTHER PUBLICATIONS

Per Sauerberg, Preben H. Olesen, Susanne Nielsen, Svend Treppendahl, Malcolm J. Sheardown, Tage Honore, Charles H. Mitch, John S. Ward, Andrew J. Pike, Frank P. Bymaster, Berry D. Sawyer and Harlan E. Shannon, Novel Functional M$_1$ Selective Muscarinic Agonists. Synthesis and Structure--ActivityRelationshipsof3--(1,2,5--Thiadiazolyl)--1,2,5, 6--tetrahydro--1--methylpyridines, J. Med. Chem. (1992), 35, pp. 2274--2283.

Philip G. Dunbar, Graham J. Durant, Zheng Fang, Yahaya F. Abuh, Afif A. El--Assadi, Dan O. Ngur, Sumudra Periyasamy, Wayne P. Hoss and Williams S. Messer, Jr., Design, Synthesis, and Neurochemical Evaluation of 5--(3--Alkyl--1, 2,4--oxadiazol--5--yl)--1,4,5,6--tetrahydropyrimidines as M$_1$ Muscarinic Receptor Agonists, J. Med. Chem. (1993), 36, pp. 842--847.

John S. Ward, Leander Merritt, David O. Calligaro, Franklin P. Bymaster, Harlan E. Shannon, Charles H. Mitch, Celia Whitesitt, David Brunsting, Malcolm J. Sheardown, Preben H. Olesen, Michael D.B. Swedberg, Lone Jeppesen, and Per Sauerberg, 1,2,5--Thiadiazole Analogues of Aceclidine as Potent m$_1$ Muscarinic Agonists, J. Med. Chem. (1998), 41, pp. 379--392.

Per Sauerberg, Lone Jeppesen, Preben H. Olesen, Thoger Rasmussen, Michael D.B. Swedberg, Malcolm J. Sheardown, Anders Fink--Jensen, Christian Thomsen, Henning Thogersen, Karin Rimvall, John S. Ward, David O. Calligaro, Neil W. DeLapp, Frank P. Bymaster and Harlan E. Shannon, Muscarinic Agonists with Antipsychotic--like Activity: Structure--Activity Relationships of 1,2,5--Thiadiazole Analogues with Functional Dopamine Antagonist Activity, J. Med. Chem. (1998), 41, pp. 4378--4384.

Lone Jeppesen, Preben H. Olesen, Lena Hansen, Malcolm J. Sheardown, Christian Thomsen, Thoger Rasmussen, Anders Fink Jensen, Michael S. Christensen, Karin Rimvall, John S. Ward, Celia Whitesitt, David O. Calligaro, Frank P. Bymaster, Neil W. DeLapp, Christian C. Felder, Harlan E. Shannon, and Per Sauerberg, 1,(1,2,5--Thiadiazol--4--yl)--4--azatricyclo[2.2.10$^{2,6}$]heptanes as New Potent Muscarinic M$_1$ Agonists: Structure--Activity Relationship for 3--Aryl--2--propyn--1--yloxy and 3--Aryl--2--propyn--1--ylthio Derivatives, J. Med. Chem. (1999), 42, pp. 1999--2006.

*Primary Examiner*—Amelia Owens
(74) *Attorney, Agent, or Firm*—Emch, Schaffer, Schaub & Porcello, Co., L.L.P.

(57) ABSTRACT

A compound of Formula (I):

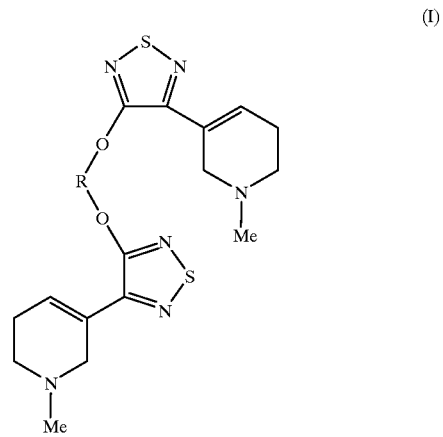

wherein R is independently selected from $(CH_2)_{9-12}$, $(CH_2CH_2)_2O$, $(CH_2CH_2)_3O_2$, $(CH_2CH_2)_4O_3$, $(CH_2CH_2)_5O_4$, $(CH_2CH_2)_6O_5$ or $(CH_2CH_2CH_2)_3O_2$; or an acid addition salt or hydrate thereof. The compounds, with improved water solubility, have unusually high affinity for muscarinic receptors, and exhibit agonist activity useful in the treatment of neurological and other disorders, in which stimulating cholinergic activity is desirable.

21 Claims, No Drawings

MUSCARINIC RECEPTOR AGONISTS

CROSS-REFERENCE TO RELATED APPLICATION

This application is a continuation-in-part of application Ser. No. 09/236,030 filed on Jan. 22, 1999 now U.S. Pat. No. 6,096,767.

FIELD OF THE INVENTION

This invention relates to muscarinic receptor ligands with agonist activity. More particularly, this invention relates to compounds based on the tetrahydropyridyl moiety with improved water solubility that have unusually high affinity for muscarinic receptors, and exhibit agonist activity useful in the treatment of neurological and other disorders, in which stimulating cholinergic activity is desirable.

BACKGROUND OF THE INVENTION

Recent advances have been made in the understanding of the cholinergic nervous system and the receptors therein. Cholinergic receptors are proteins embedded in the cell membrane that respond to the chemical acetylcholine. Cholinergic receptors are subdivided into the nicotinic and muscarinic receptor families, and muscarinic receptors represent a family of five subtypes.

Muscarinic receptors mediate a variety of physiological responses to the neurotransmitter acetylcholine in the central and peripheral nervous systems. $M_1$ muscarinic receptors play a role in learning and memory function in the brain and regulate gastric acid secretion in the stomach. $M_2$ receptors regulate acetylcholine release in the central nervous system and control cardiac muscle contraction in the heart. Acetylcholine stimulates smooth muscle contraction in a variety of tissues and promotes secretion from exocrine glands. These effects are mediated by $M_3$ receptors. Though less well characterize d pharmacologically, $M_4$ receptors appear to play a role in the perception of pain, and $M_5$ receptors may regulate dopaminergic activity in the brain.

Despite the wealth of knowledge about muscarinic receptor subtypes, relatively few selective ligands are available to characterize muscarinic receptor subtypes. Consequently, the tendency for ligands to bind indiscriminately to muscarinic receptor subtypes has made difficult the development of drugs that are muscarinic receptor subtype selective.

In view of the foregoing, it would be desirable to provide such compounds, particularly so side effects are minimized during treatment of the conditions noted above. It is an object of the present invention to provide compounds having muscarinic receptor affinity and activity.

It is another object of the present invention to provide compounds having improved muscarinic receptor selectivity profiles.

Another object of the present invention is to provide compounds having improved water solubility and high potency.

It is another object of the present invention to provide pharmaceutical composition comprising compounds of the present invention, as active ingredients.

SUMMARY OF THE INVENTION

The present invention relates to a series of compounds based on the tetrahydropyridyl moiety with improved water solubility that possess an unusually high affinity for muscarinic receptors . Such compounds are contemplated as being useful in the treatment of neurological and other disorders, in which regulating cholinergic activity is desirable.

According to one aspect of the present invention, there is provided a compound of Formula I:

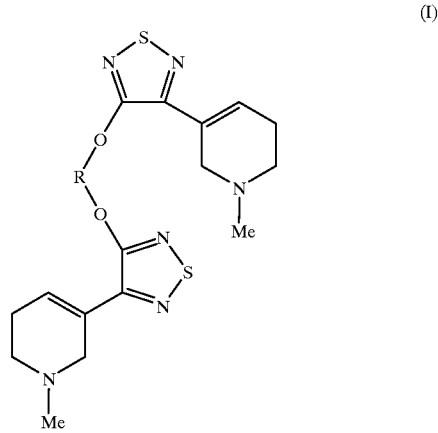

(I)

Wherein R is independently selected from $(CH_2)_{9-12}$, $(CH_2CH_2)_2O$, $(CH_2CH_2)_3O_2$, $(CH_2CH_2)_4O_3$, $(CH_2CH_2)_5O_4$, $(CH_2CH_2)_6O_5$ or $(CH_2CH_2CH_2)_3O_2$; or an acid addition salt or hydrate thereof.

According to another aspect of the present invention there is provided a pharmaceutical composition comprising compounds of Formula (I) and a pharmaceutically acceptable carrier.

DETAILED DESCRIPTION OF THE PREFERRED EMBODIMENTS

The invention relates to bis-alkyloxy-1,2,5-thiadiazole derivatives of 1,2,5,6-tetrahydropyridine that bind to and activate muscarinic receptors. The compounds incorporate two functional muscarinic agonists into the same molecule with an alkyloxy linkage. More particularly, the present invention is directed to compounds of Formula I:

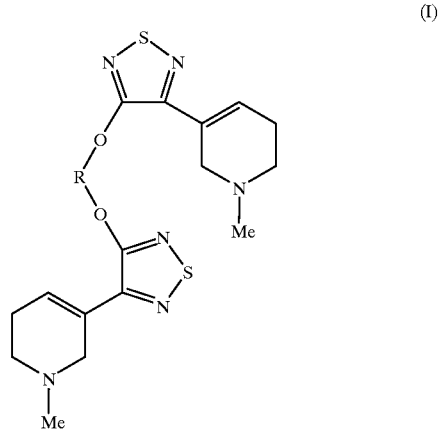

(I)

Wherein R is independently selected from $(CH_2)_{9-12}$, $(CH_2CH_2)_2O$, $(CH_2CH_2)_3O_2$, $(CH_2CH_2)_4O_3$, $(CH_2CH_2)_5O_4$, $(CH_2CH_2)_6O_5$ or $(CH_2CH_2CH_2)_3O_2$; or an acid addition salt or hydrate thereof.

The compounds of Formula (I), 2, 2'-bis-{[3-(1-methyl-1,2,5, 6-tetrahydropyrid-3-yl)-1,2,5-thiadiazol-4-yloxy] ethyloxy}-diethylether and 1,1 2-bis-[3-(1-methyl-1,2,5,6- tetrahydropyrid-3-yl)-1,2,5-thiadiazol-4-yloxy]-dodecane, exhibit very high affinity for muscarinic receptors as compared to the parent compound xanomeline. In addition, the compounds appear to interact with multiple $M_2$ receptors expressed in A9 L cells. It is believed that compounds of Formula (I) may act as agonists at muscarinic receptors coupled to the inhibition of adenylyl cyclase activity.

TABLE 1

| Ligand/Linkage | M1 Receptors $K_i$ (nM) | % High affinity | M2 Receptors $K_h$ (pM) | $K_1$ (nM) |
| --- | --- | --- | --- | --- |
| Xanomeline | 82 ± 6.7 | 26 ± 8.5 | 23 ± 16 | 32 ± 12 |
| $(CH_2)_6$ | 0.61 ± 0.18 | 18 ± 4.5 | 0.0086 ± 0.0069 | 0.28 ± 0.020 |
| $(CH_2)_8$ | 0.19 ± 0.040 | 40 ± 11 | 58 ± 56 | 0.38 ± 0.15 |
| $(CH_2)_{10}$ | 0.23 ± 0.10 | 26 ± 3.1 | 3.1 ± 2.4 | 0.23 ± 0.040 |
| $(CH_2CH_2)_4O_3$ | 0.12 ± 0.057 | — | — | — |

It was heretofore believed that as the length of the alkoxy chain increases agonist activity decreases. As reported in the Journal of Medicinal Chemistry, 1993, Vol. 36, No. 7, pages 843–844, increasing the length of the alkyl chain on the 1,2,4-oxadiazole ring of 1,4,5, 6-tetrahydropyrimidine dramatically decreased activity in the phosphoinositide metabolism assay. Again these data are consistent with similar observations in 1,2,4-oxadiazole derivatives of 1,2,5, 6-tetrahydro-1-methylpyridineand quinuclidine where increasingthe length of the 3-alkyl substituent led to compounds with higher affinity yet lower agonist activity. As shown in Tables 1 and 2, it has been surprisingly found that compounds of Formula II with increasing alkoxy chains displayed $M_1$ agonist efficacy comparable to xanomeline, yet with higher potency and higher affinity for $M_1$ receptors.

The receptor binding properties and agonist activity of bisthiadiazole derivatives, (Formula (II)), at $M_1$ muscarinic receptors expressed in A9 L cells is provided below in Table 2. PI metabolism represents the percentage stimulation above basal levels at 100 μM expressed relative to the carbachol response (100%). Full dose-response curves were obtained for a few compounds. The data in Table 2 below represents the mean (±s.e.m.) from two to five assays for each compound.

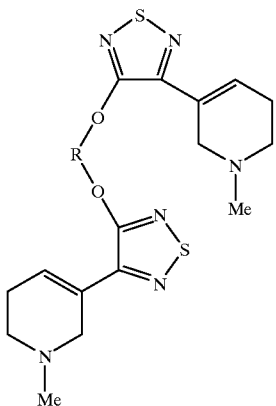

(II)

wherein R is a linkage independently selected from $(CH_2)_{9-12}$, $(CH_2)_3$, $(CH_2)_4$, $(CH_2)_5$, $(CH_2)_6$, $(CH_2)_7$, $(CH_2)_8$, $(CH_2)_9$, $(CH_2)_{10}$, $(CH_2)_{12}$ and $(CH_2CH_2)_4O_3$.

TABLE 2

| Compound/Linkage | PI metabolism (at 100 μM) | $EC_{50}$ (μm) | $S_{max}$ |
| --- | --- | --- | --- |
| Xanomeline | n.d. | 5.7 ± 2.3 | 180 ± 24% |
| $(CH_2)_2$ | 50 ± 14% | — | — |
| $(CH_2)_3$ | 21 ± 2.6% | — | — |
| $(CH_2)_4$ | 21 ± 1.9% | — | — |
| $(CH_2)_5$ | -1.0 ± 1.8% | — | — |
| $(CH_2)_6$ | 18 ± 0.06% | — | — |
| $(CH_2)_7$ | -3.0 ± 3.4% | — | — |
| $(CH_2)_9$ | 8.2 ± 1.4% | — | — |
| $(CH_2)_9$ | 27 ± 6.2% | 0.72 ± 0.37 | 140 ± 34% |
| $(CH_2)_{10}$ | 76 ± 11% | — | — |
| $(CH_2)_{12}$ | 84 ± 9.9% | 0.34 ± 0.19 | 190 ± 61% |
| $(CH_2CH_2)_4O_3$ | — | 0.0085 ± 0.0012 | 250 ± 36% |

The compounds of Formula (I) are preferably isolated in substantially pure form.

The binding profiles of the compounds of Formula (I) indicate their utility as pharmaceuticals useful for the treatment of various conditions in which the use of a muscarinic receptor ligand is indicated. More particularly, the compounds of Formula (I) have been found to mimic acetylcholine function via an action at muscarinic receptors and are therefore of potential use in the treatment of pain, Alzheimer's disease and other disorders involving cholinergic deficits. Furthermore, it has been found that the inclusion of heteroatoms in the alkyl chain seems to improve the water solubility of the compounds. In addition, agonist activity is enhanced relative to the straight chain derivatives.

The compositions where $R=(CH_2)_{10}$ and $R=(CH_2)_{12}$ were compared to the composition where $R=(CH_2CH_2)_4O_3$ Table 3 below shows water solubilities versus receptor binding properties and agonist activities of bisthiadiazole derivatives at $M_1$ muscarinic receptors expressed in A9 L cells. Binding data ($K_i$ values) were from competition assays utilizing [$^3$H]-(R)-QNB as the radioligand. PI metabolism represents the percentage stimulation above basal levels at 100 μM expressed relative to the carbachol response (100%). Full does-response curves were also obtained for the composition where $R=(CH_2)_{12}$ and compound d. Data represent the mean (±s.e.m.) from two to five assays for each compound. (n.d., not determined; r.t., room temperature)

TABLE 3

| Compound | Solubility (deionized water, r.t.) | Solubility (KH buffer, r.t.) | $M_1$ receptors $K_1$ (nM) | PI metabolism (at 100 µm) | $EC_{50}$ (nM) | Smax (%) |
|---|---|---|---|---|---|---|
| $(CH_2)_9$ | | | 0.84 ± 0.60 | 27 ± 6.2% | 720 ± 370 | 140 ± 34 |
| $(CH_2)_{10}$ | 25 mg/ml | 4.0 µg/ml | 0.23 ± 0.10 | 76 ± 11% | n.d. | n.d. |
| $(CH_2)_{12}$ | 20 mg/ml | 1.7 µg/ml | 1.6 ± 0.51 | 84 ± 9.9% | 340 ± 190 | 190 ± 61 |
| $(CH_2CH_2)_4O_3$ | >1 g/ml | 20 mg/ml | 0.12 ± 0.057 | | 8.5 ± 1.2 | 250 ± 36 |

The present invention also provides pharmaceutical compositions, which comprise compounds of Formula (I) or pharmaceutically acceptable salts thereof, and pharmaceutically acceptable carriers. The pharmaceutical composition may be in the form of patches, tablets, capsules, powders, granules, lozenges, suppositories, reconstitutable powders or liquid preparations such as oral or sterile parenteral solutions or suspensions. The pharmaceutical composition includes compounds of Formula (I) of a pharmaceutically acceptable level of purity excluding normal pharmaceutical additives such as dilutents and carriers, and including no material considered toxic at normal dosage levels. A pharmaceutically acceptable level of purity will generally be at least 90% excluding normal pharmaceutical additives, preferably 95%, more preferably 97% and still more preferably 99%.

Sauerberg et al., Journal Medicinal Chemistry, 1992, Vol. 35, page 2274, reported the synthesis and SAR of potent ligands for $M_1$ receptors based on the 1,2,5-thiadiazolyl-tetrahydropyridine moieties. In accordance with the present invention, it was found that if two 1,2,5-thiadiazolyltetrahydropyridine moieties are tethered by spacers of varied length and rigidity, in a single structure, the binding affinity of the resultant bis ligands is enhanced. By varying the length of the alkyl chain and also replacing some of the carbons with heteroatoms like N, O or S, structure activity relationship can be established. The two ligands in the same molecule may either bind in the pockets of two proximal receptors or in two pockets of the same receptor molecule.

The compounds of Formula (I) can be prepared using processes well known in the art.

The following are detailed examples of a preferred process to prepare compounds of Formula (I). It will be understood that the following example is not intended to limit the scope of the invention.

EXAMPLE 1

3-(3-chloro-1,2,5-thiadiazol-4-yl)pyridine (compound 1) was synthesized from 3-pyridinecarboxaldehyde following, except with slight modification, from the published procedure as provided in Sauerberg et al., Journal Medicinal Chemistry, 1992, Vol.35, Page 2274. 3-(3-chloro-1,2,5-thiadiazol-4-yl)pyridine was reacted with a diol (compound 2, wherein n=6, 7, 8, 9, 10 or 12) in the presence of sodium hydride in refluxing THF to yield bis[3-(pyridin-3-yl)-1,2,5-thiadiazol-4-yl]alkyl-diethers (compound 3, wherein n=wherein n=6, 7, 8, 9, 10 or 12) in 75–90% yield. These diethers were treated with excess methyl iodide in acetone or chloroform to give bis-quaternary ammonium iodides (compound 4, wherein n=6, 7, 8, 9, 10 or 12) in 96–100% yield. The quaternary salts were then treated with 5 equivalents of sodium borohydride in a mixture of methanol and chloroform to yield the compounds 5, wherein n=6, 7, 8, 9, 10 or 12 in 50–60% yield. Dry hydrogen chloride gas was then bubbled through the methanolic solution of compounds 5 at 0° C. to give compounds 6, wherein n=6, 7, 8, 9, 10 or 12 in 95–100% yield.

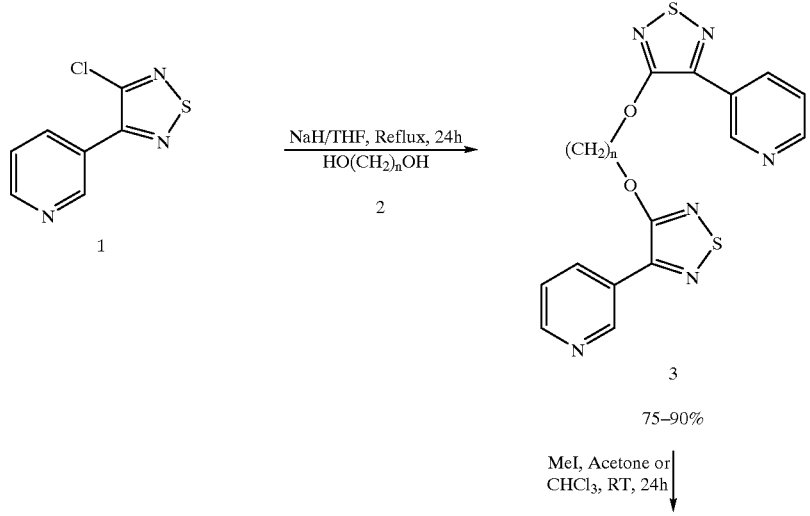

-continued

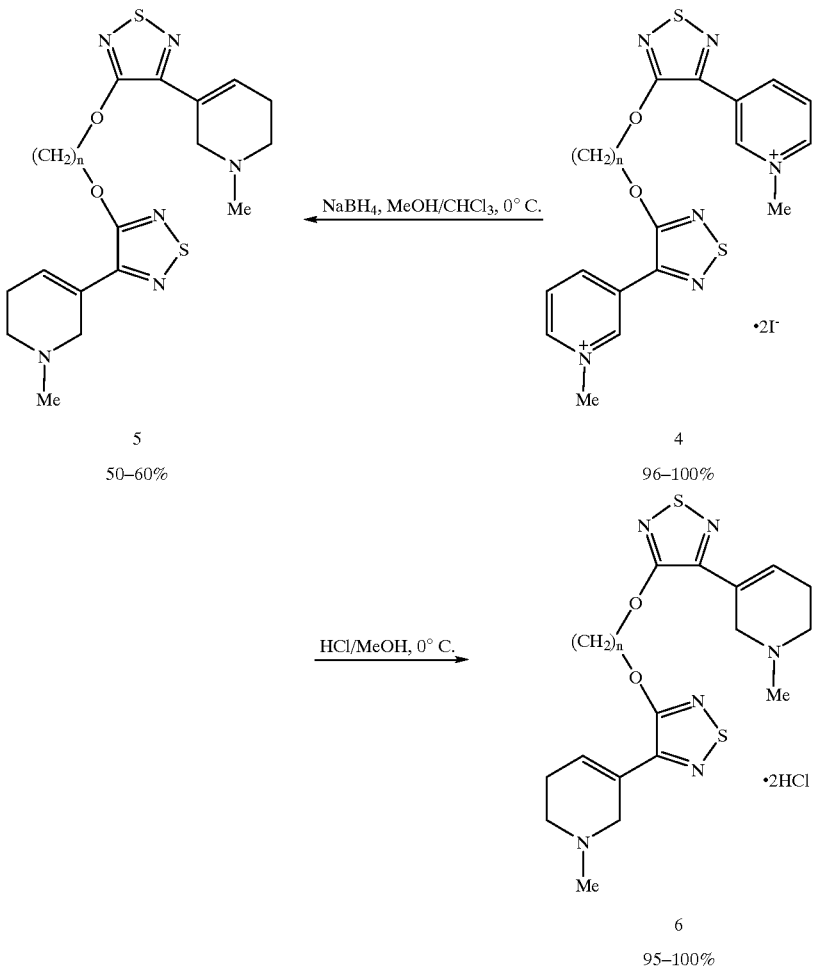

wherein n = 2, 3, 4, 5, 6, 7, 8, 9, 10 and 12.

EXAMPLE 2
2,2'-bis{[3-(pyrid-3-y)-1, 2, 5-thadiazol-4-yloxy]ethyloxy}diethylether A suspension of 60% NaH in mineral oil (0.2 g, 5 mmol) was washed with hexane and suspended in THF (20 ml). To this suspension was added tetra(ethylene glycol) (196 mg, 1 mmol) and the reaction mixture was refluxed for 1 h. Then a solution of 3-(3-chloro-1,2, 5-thiadiazol-4-yl)pyridine (500 mg, 2.53 mmol) in THF (15 ml) was added and the reaction mixture was refluxed for 24 h. The solvent was removed under reduced pressure and ice cold water was added to the residue, then the aqueous solution was extracted with $CHCl_3$. The organic layer was washed with water and dried over $Na_2SO_4$. After removing the solvent, the oily crude compound was obtained (500 mg, 97% yield).

Quaternary salt of 2,2'-bis{[3-(pyrid-3-yl)-1,2,5-thiadiazol-4-yloxy]ethyloxy}diethylether To a solution of 2,2'-bis{[3-(pyrid-3-yl)-1,2,5-thiadiazol-4-yloxy]ethyloxy}diethylether (1 mmol) in acetone (25 ml) was added excess $CH_3I$ (3 ml, 48 mmol) and the solution was stirred for 36 h at room temperature. The precipitate was filtered, washed with acetone and dried to give the quaternary salt of 2,2'-bis{[3-(pyrid-3-yl)-1,2, 5-thiadiazol-4-yloxy]ethyloxy}diethylether (0.79 g, 99% yield).

2,2'-bis{[3-(1-methyl-1,2,5,6-tetrahydropyrid-3-yl)-1,2,5-thiadiazol-4-yloxy]ethyloxy}diethylether dihydrochloride (compound d)

The pyridinium iodide (0.75 g, 0.94 mmol) was dissolved in a mixture of $CHCl_3$ (15 ml) and MeOH (15 ml). The solution was cooled to 0–5° C. and $NaBH_4$ (164 mg, 4.3 mmol) was added to the reaction mixture. It was stirred at 0–5° C. for 2 h. Then cold $H_2O$ and more $CHCl_3$ (30 ml) were added to the reaction mixture and the organic layer was separated, washed with water and dried. The solvent was removed under reduced pressure and the residue was chromatographed on a column of silica gel. (Eluent : 1:10 MeOH/$CHCl_3$). The cleaned-up compound was dissolved in MeOH (10 ml) and the solution was cooled to 0° C. Then dry HCl was bubbled through the solution for 3 minutes and cold ether was added to precipitate the dihydrochloride salt. The precipitated solid was filtered, washed with ether and dried to give the title compound (300 mg, 51% yield).

mp: 69.2–70.8° C., $^1$H NMR ($H_2O$): δ 2.5 (m, 4H), 2.81 (s, 6H, N-Me), 3.04 (m, 2H), 3.5 (m, 10H), 3.75 (m, 6H), 4.25 (m, 2H), 4.37 (s, 4H, $CH_2$) and 7.0 (m, 2H, vinylic). analysis calculated for $C_{24}H_{38}N_6O_5S_2Cl_2·H_2O$; C, 44.79; H, 6.26; N, 13.06; found: C, 44.94; H, 6.09; N, 12.85.

The following compounds were made in the same manner as described for compound d above, using the appropriate glycol:

1,2-Bis[3-(1-methyl-1,2,5,6-tetrahydropyrid-3-yl)-1,2,5-thiadiazol-4-yloxy]ethane dihydrochloride (compound a): m.p. 217–18° C.; analysis calculated for $C_{18}H_{26}N_6O_2S_2Cl_2\cdot H_2O$: C, 42.27; H, 5.52; N, 16.43; found: C, 42.23; H, 5.42; N, 16.38.

2,2'-Bis[3-(1-methyl-1,2,5,6-tetrahydropyrid-3-yl)-1,2,5-thiadiazol-4-yloxy]diethylether dihydrochloride (compound b): m.p. 191.7–193.8° C.; analysis calculated for $C_{20}H_{30}N_6O_3S_2Cl_2\cdot H_2O$: C, 43.24; H, 5.81; N, 15.13; found: C, 43.23; H, 5.85; N, 15.02.

1,2-Bis{[3-(1-methyl-1,2,5,6-tetrahydropyrid-3-yl)-1,2,5-thiadiazol-4-yloxy]ethyloxy}ethane dihydrochloride (compound c): m.p. 63.8–65.4° C.; analysis calculated for $C_{22}H_{34}N_6O_4S_2Cl_2\cdot H_2O$: C, 44.07; H, 6.05; N, 14.02; found: C, 43.99; H, 6.27; N, 13.93.

Penta(ethylene glycol)-di-[3-(1-methyl-1,2,5,6-tetrahydropyrid-3-yl)-1,2,5-thiadiazol-4-yl]ether dihydrochloride (compound e): m.p. 90.6–92.4° C.; analysis calculated for $C_{26}H_{42}N_6O_6S_2Cl_2\cdot 0.5H_2O$: C, 46.01; H 6.39; N, 12.38; found: C, 45.80; H, 6.44; N, 12.31.

1,3-Bis{[3-(1-methyl-1,2,5,6-tetrahydropyrid-3-yl)-1,2,5-thiadiazol-4-yloxy]propyloxy} propane dihydrochloride (compound f): semi-solid, hygroscopic; analysis calculated for $C_{25}H_{38}N_6O_4S_2Cl_2\cdot 2H_2O$: C, 45.52; H, 6.72; N, 12.74; found: C, 45.32; H, 6.75; N, 12.46.

Hexa(ethylene glycol)-di-[3-(1-methyl-1,2,5,6-tetrahydropyrid-3-yl)-1,2,5-thiadiazol-4-yl]ether dihydrochloride (compound g): semi-solid, hygroscopic; analysis calculated for $C_{28}H_{46}N_6O_7S_2Cl_2\cdot 2H_2O$: C, 44.86; H, 6.72; N, 11.21; found: C, 45.14; H, 6.53; N, 10.90.

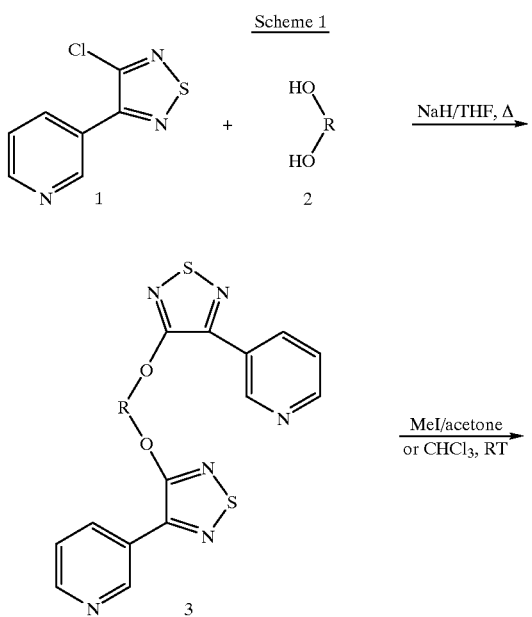

Scheme 1

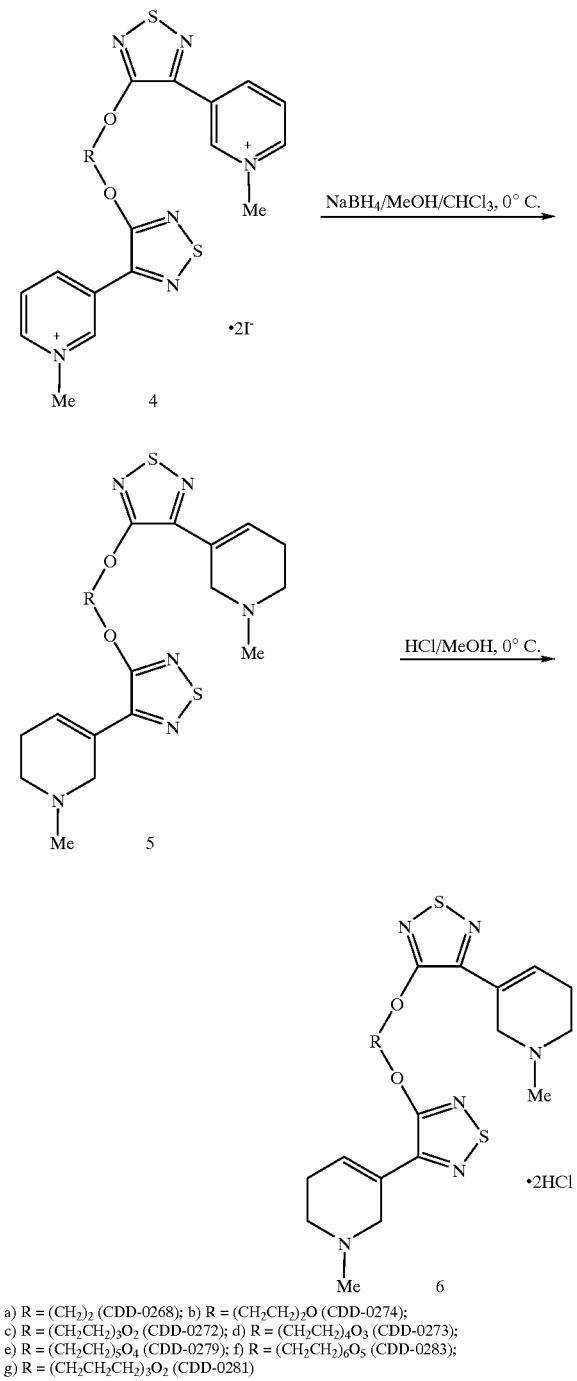

a) R = $(CH_2)_2$ (CDD-0268); b) R = $(CH_2CH_2)_2O$ (CDD-0274);
c) R = $(CH_2CH_2)_3O_2$ (CDD-0272); d) R = $(CH_2CH_2)_4O_3$ (CDD-0273);
e) R = $(CH_2CH_2)_5O_4$ (CDD-0279); f) R = $(CH_2CH_2)_6O_5$ (CDD-0283);
g) R = $(CH_2CH_2CH_2)_3O_2$ (CDD-0281)

In view of the detailed description provided herein, it will be appreciated by one skilled in the art that the above bis-ligand methodology can include, but not be limited to, other known and potential muscarinic ligands such as tetrahydropyrimidine-oxadiazoles, tetrahydropyrimidine-thiadiazoles, quinuclidine-thiadiazoles, and the like.

The patents, documents and publications described herein are hereby incorporated by reference.

Having described presently preferred embodiments of the invention, it is to be understood that it may be otherwise embodiment within the scope of the appended claims.

We claim:
1. A compound of Formula (I):

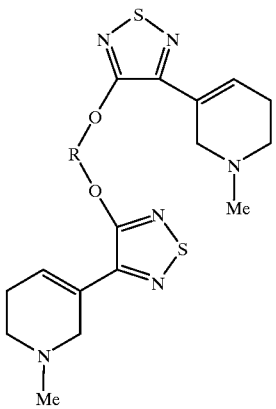

wherein R is independently selected from $(CH_2)_{9-12}$, $CH_2CH_2OCH_2CH_2$, $CH_2CH_2OCH_2CH_2OCH_2CH_2$, $CH_2CH_2OCH_2CH_2OCH_2CH_2OCH_2CH_2$, $CH_2CH_2OCH_2CH_2OCH_2CH_2OCH_2CH_2OCH_2CH_2$, $CH_2CH_2OCH_2CH_2OCH_2CH_2OCH_2CH_2OCH_2CH_2OCH_2CH_2$, $CH_2CH_2CH_2OCH_2CH_2CH_2OCH_2CH_2CH_2$; or an acid addition salt or hydrate thereof.

2. The compound of claim 1 in which $R=(CH_2)_9$.
3. The compound of claim 1 in which $R=(CH_2)_{10}$.
4. The compound of claim 1 in which $R=(CH_2)_{12}$.
5. The compound of claim 1 in which $R=(CH_2CH_2)_2O$ and has the formula

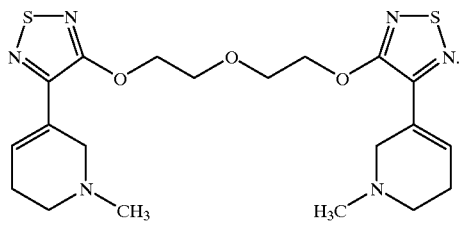

6. The compound of claim 1 in which $R=(CH_2CH_2)_3O_2$ and has the formula

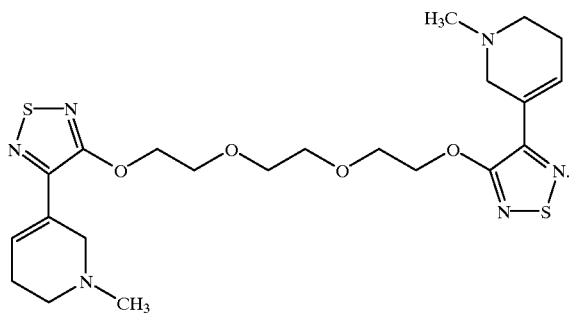

7. The compound of claim 1 in which $R=(CH_2CH_2)_4O_3$ and has the formula

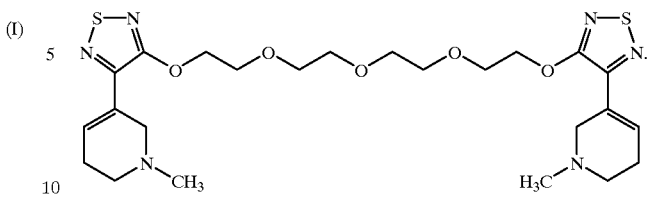

8. The compound of claim 1 in which $R=(CH_2CH_2)_5O_4$ and has the formula

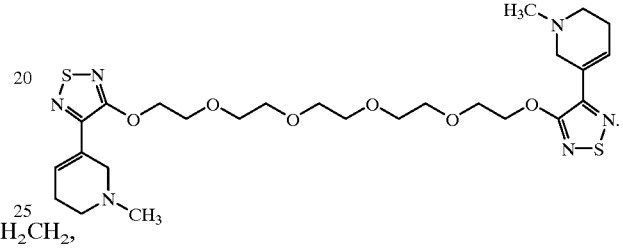

9. The compound of claim 1 in which $R=(CH_2CH_2)_6O_5$ and has the formula

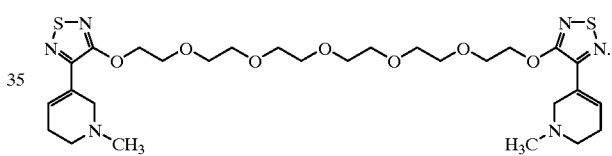

10. The compound of claim 1 in which $R=(CH_2CH_2CH_2)_3O_2$ and has the formula

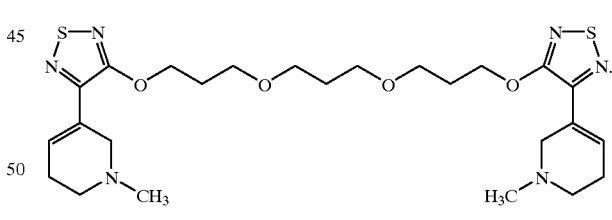

11. A pharmaceutical composition, comprising a therapeutically effective amount of a compound according to claim 1, and a pharmaceutically acceptable carrier.

12. A method for the treatment of neurological and other disorders, in which stimulating cholinergic activity is desirable, comprising administering an effective amount of a muscarinic receptor ligand exhibiting agonist activity comprising a compound of Formula (I):

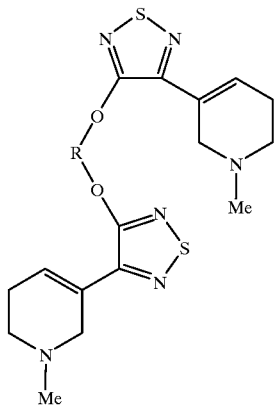

(I)

wherein R is independently selected from $(CH_2)_{9-12}$, $[(CH_2CH_2)_2O$, $(CH_2CH_2)_3O_2$, $(CH_2CH_2)_4O_3$, $(CH_2CH_2)_5O_4$, $(CH_2CH_2)_6O_5$ or $(CH_2CH_2CH_2)_3O_2;]$ $CH_2CH_2OCH_2CH_2$, $CH_2CH_2OCH_2CH_2OCH_2CH_2$, $CH_2CH_2OCH_2CH_2OCH_2CH_2OCH_2CH_2$, $CH_2CH_2OCH_2CH_2OCH_2CH_2OCH_2CH_2OCH_2CH_2$, $CH_2CH_2OCH_2CH_2OCH_2CH_2OCH_2CH_2OCH_2CH_2OCH_2CH_2$, $CH_2CH_2CH_2OCH_2CH_2CH_2OCH_2CH_2CH_2$; or an acid addition salt or hydrate thereof.

13. The method of claim 10 in which R=$(CH_2)_9$.
14. The method of claim 10 in which R=$(CH_2)_{10}$.
15. The method of claim 10 in which R=$(CH_2)_{12}$.
16. The compound of claim 10 in which R=$(CH_2CH_2)_2O$ and has the formula

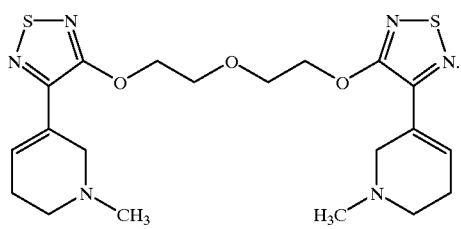

17. The compound of claim 10 in which R=$(CH_2CH_2)_3O_2$ and has the formula

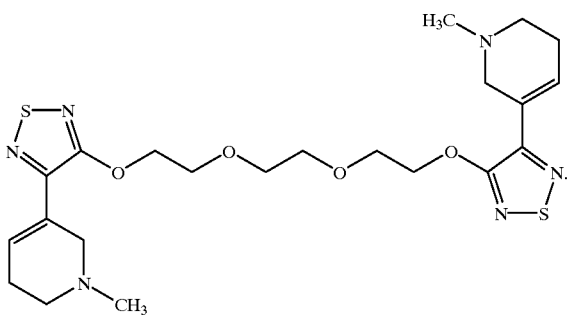

18. The compound of claim 10 in which R=$(CH_2CH_2)_4O_3$ and has the formula

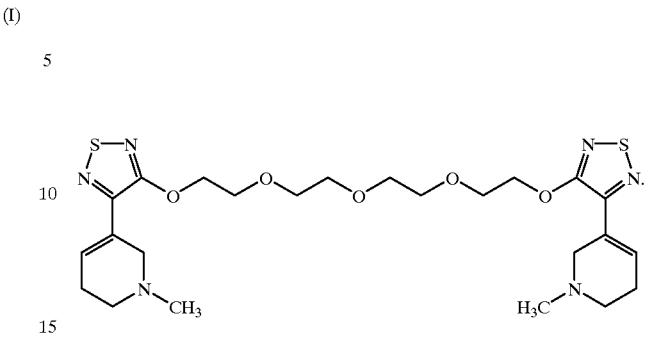

19. The compound of claim 10 in which R=$(CH_2CH_2)_5O_4$ and has the formula

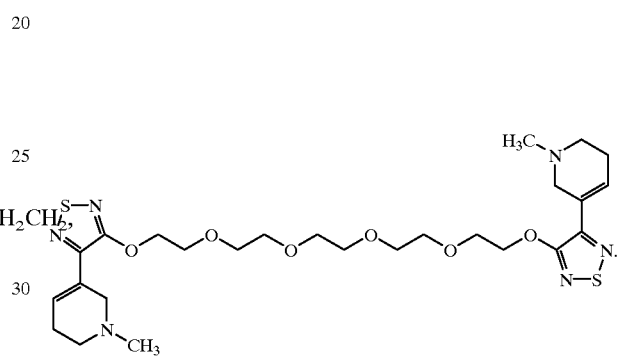

20. The compound of claim 10 in which R=$(CH_2CH_2)_6O_5$ and has the formula

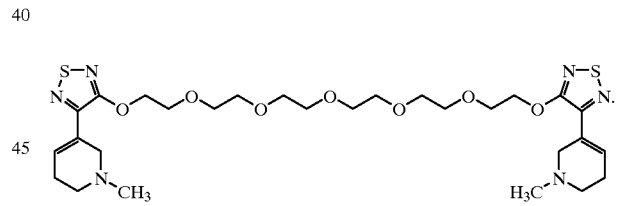

21. The compound of claim 10 in which R=$(CH_2CH_2CH_2)_3O_2$ and has the formula

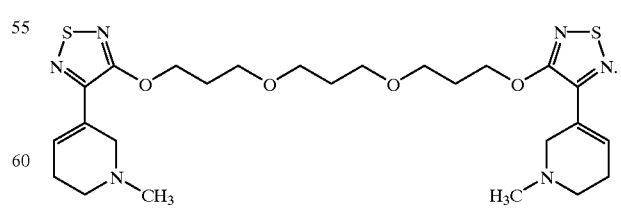

* * * * *

UNITED STATES PATENT AND TRADEMARK OFFICE
CERTIFICATE OF CORRECTION

PATENT NO.    : 6,211,204 B1
DATED         : April 3, 2001
INVENTOR(S)   : William S. Messer, Yang Cao & Walajapet G. Rajeswaran Page 1 of 1

It is certified that error appears in the above-identified patent and that said Letters Patent is hereby corrected as shown below:

<u>Column 13, claim 12,</u>
Lines 22-23, please delete bracketed chemical compound "[$(CH_2CH_2)_2O$, $(CH_2Ch_2)_3O_2$, $(CH_2CH_2)_4O_3$, $(CH_2CH_2)_5O_4$, $(CH_2CH_2)_6O_5$ OR $(CH_2CH_2CH_2)_3O_2$;]".

Signed and Sealed this

Twenty-fifth Day of December, 2001

Attest:

JAMES E. ROGAN
*Attesting Officer*                *Director of the United States Patent and Trademark Office*